US011915605B2

(12) United States Patent
Tzenios

(10) Patent No.: US 11,915,605 B2
(45) Date of Patent: Feb. 27, 2024

(54) KETOGENIC DIET RECOMMENDATION TO A USER BASED ON A BLOOD LOW-DENSITY LIPOPROTEIN (LDL) LEVEL AND A BLOOD C-REACTIVE PROTEIN LEVEL AND/OR A BLOOD ERYTHROCYTE SEDIMENTATION RATE (ESR) THEREOF

(71) Applicant: Nicolas Tzenios, London (GB)

(72) Inventor: Nicolas Tzenios, London (GB)

( * ) Notice: Subject to any disclaimer, the term of this patent is extended or adjusted under 35 U.S.C. 154(b) by 288 days.

(21) Appl. No.: 16/655,293

(22) Filed: Oct. 17, 2019

(65) Prior Publication Data

US 2021/0118327 A1    Apr. 22, 2021

(51) Int. Cl.
*G09B 19/00* (2006.01)
*G16H 20/60* (2018.01)

(52) U.S. Cl.
CPC ......... *G09B 19/0092* (2013.01); *G16H 20/60* (2018.01)

(58) Field of Classification Search
CPC ..... G09B 19/0092; G16H 20/60; G16H 50/20
See application file for complete search history.

(56) References Cited

U.S. PATENT DOCUMENTS

| | | | |
|---|---|---|---|
| 9,011,153 B2 | 4/2015 | Bennett et al. | |
| 10,262,553 B2 | 4/2019 | Benefield et al. | |
| 2013/0216982 A1* | 8/2013 | Bennett | A61B 5/4866 434/127 |
| 2014/0017337 A1 | 1/2014 | Amoruso | |
| 2015/0194071 A1 | 7/2015 | Bennett et al. | |
| 2016/0371998 A1 | 12/2016 | Fazeel | |
| 2017/0053551 A1 | 2/2017 | Prisk | |
| 2017/0266148 A1 | 9/2017 | D'Agostino et al. | |
| 2017/0332951 A1 | 11/2017 | Ahmad et al. | |
| 2018/0374385 A1 | 12/2018 | Benefield et al. | |
| 2019/0096281 A1 | 3/2019 | Ahmad et al. | |
| 2019/0295440 A1 | 9/2019 | Hadad | |

FOREIGN PATENT DOCUMENTS

| | | |
|---|---|---|
| KR | 20160015069 A | 2/2016 |
| WO | 1996039073 A1 | 12/1996 |
| WO | 2013085047 A1 | 6/2013 |
| WO | 2014153416 A1 | 9/2014 |
| WO | 2018186481 A1 | 10/2018 |

* cited by examiner

*Primary Examiner* — Peter R Egloff
(74) *Attorney, Agent, or Firm* — LEGALFORCE RAPC WORLDWIDE

(57) ABSTRACT

A method includes executing a diet recommendation process through a server to baseline an optimized diet to be recommended to a user with an elevated blood LDL level of 100-150 mg/dL and an elevated C-reactive protein level of >3 mg/L and/or an elevated ESR of >20 mm/hr based on performing statistical analyses on investigation data of a population of human subjects, and to modify a composition of the baselined optimized diet to be recommended to the user based on determining that adhering to the baselined optimized diet results in an increase in the elevated blood LDL level of the user accompanied by a decrease in the elevated C-reactive protein level and/or a decrease in the elevated ESR thereof and one or more parameter(s) of the user with reference to an additionally baselined optimal blood LDL level and an optimal blood C-reactive protein level and/or an optimal blood ESR.

4 Claims, 3 Drawing Sheets

KETOGENIC DIET RECOMMENDATION TO A USER BASED ON A BLOOD LOW-DENSITY LIPOPROTEIN (LDL) LEVEL AND A BLOOD C-REACTIVE PROTEIN LEVEL AND/OR A BLOOD ERYTHROCYTE SEDIMENTATION RATE (ESR) THEREOF

FIELD OF TECHNOLOGY

This disclosure relates generally to health-related diet recommendation and, more particularly, to a method, a system and/or a device for a ketogenic diet recommendation to a user based on a blood low-density lipoprotein (LDL) level and a blood C-reactive protein level and/or a blood Erythrocyte Sedimentation Rate (ESR) thereof.

BACKGROUND

A ketogenic diet involving a reduced carbohydrate intake and substitution of carbohydrates with fat may be recommended to weight loss enthusiasts. A body of a weight loss enthusiast under the ketogenic diet may experience ketosis, a state in which fats are burned instead of glucose for energy, especially during periods of low blood sugar. While adherence to the ketogenic diet may help the weight loss enthusiast maintain a healthy Body Mass Index (BMI) over the long term, composition of said ketogenic diet may be limited in terms of modifiability, especially when a plethora of health related issues with respect to the weight loss enthusiast is concerned.

SUMMARY

Disclosed are a method, a system and/or a device for a ketogenic diet recommendation to a user based on a blood low-density lipoprotein (LDL) level and a blood C-reactive protein level and/or a blood Erythrocyte Sedimentation Rate (ESR) thereof.

In one aspect, a method includes executing a diet recommendation process through a server, and in accordance with the executed diet recommendation process, baselining, through the server, an optimized diet to be recommended to a user with an elevated blood low-density lipoprotein (LDL) level of 100-150 milligrams per deciliter (mg/dL) and an elevated blood C-reactive protein level of >3 mg/L and/or an elevated blood Erythrocyte Sedimentation Rate (ESR) of >20 millimeters per hour (mm/hr) based on performing statistical analyses on investigation data of a population of human subjects with elevated blood LDL levels of 100-150 mg/dL and elevated blood C-reactive protein levels of >3 mg/L and/or elevated blood ESRs of >20 mm/hr to determine that adhering to the optimized diet leads to increasing blood LDL levels for the population accompanied by decreasing blood C-reactive protein levels and/or decreasing blood ESRs.

In accordance with the executed diet recommendation process, the method also includes additionally baselining, through the server, an optimal blood LDL level and an optimal blood C-reactive protein level and/or an optimal blood ESR based on the performance of the statistical analyses, determining, through the server, that adhering to the baselined optimized diet to be recommended to the user results in an increase in the elevated blood LDL level of the user accompanied by a decrease in the elevated blood C-reactive protein level and/or a decrease in the elevated blood ESR thereof, and modifying, through the server, a composition of the baselined optimized diet to be recommended to the user based on the determined increase in the elevated blood LDL level of the user accompanied by the decrease in the elevated blood C-reactive protein level and/or the decrease in the elevated blood ESR thereof and one or more parameter(s) of the user with reference to the additionally baselined optimal blood LDL level and the optimal blood C-reactive protein level and/or the optimal blood ESR.

In another aspect, a server includes a memory including instructions associated with a diet recommendation process, and a processor configured to execute the instructions associated with the diet recommendation process to baseline an optimized diet to be recommended to a user with an elevated blood LDL level of 100-150 mg/dL, and an elevated blood C-reactive protein level of >3 mg/L and/or an elevated blood ESR of >20 mm/hr based on performing statistical analyses on investigation data of a population of human subjects with elevated blood LDL levels of 100-150 mg/dL and elevated blood C-reactive protein levels of >3 mg/L and/or elevated blood ESRs of >20 mm/hr to determine that adhering to the optimized diet leads to increasing blood LDL levels for the population accompanied by decreasing blood C-reactive protein levels and/or decreasing blood ESRs.

The processor is also configured to execute the instructions associated with the diet recommendation process to additionally baseline an optimal blood LDL level and an optimal blood C-reactive protein level and/or an optimal blood ESR based on the performance of the statistical analyses, to determine that adhering to the baselined optimized diet to be recommended to the user results in an increase in the elevated blood LDL level of the user accompanied by a decrease in the elevated blood C-reactive protein level and/or a decrease in the elevated blood ESR thereof, and to modify a composition of the baselined optimized diet to be recommended to the user based on the determined increase in the elevated blood LDL level of the user accompanied by the decrease the elevated blood C-reactive protein level and/or the decrease in the elevated blood ESR thereof and one or more parameter(s) of the user with reference to the additionally baselined optimal blood LDL level and the optimal blood C-reactive protein level and/or the optimal blood ESR.

In yet another aspect, a non-transitory medium, readable through a server and including instructions embodied therein that are executable through the server, includes instructions to execute a diet recommendation process through the server, and, in accordance with the executed diet recommendation process, instructions to baseline an optimized diet to be recommended to a user with an elevated blood LDL level of 100-150 mg/dL and an elevated blood C-reactive protein level of >3 mg/L and/or an elevated blood ESR of >20 mm/hr based on performing statistical analyses on investigation data of a population of human subjects with elevated blood LDL levels of 100-150 mg/dL and elevated blood C-reactive protein levels of >3 mg/L and/or elevated blood ESRs of >20 mm/hr to determine that adhering to the optimized diet leads to increasing blood LDL levels for the population accompanied by decreasing blood C-reactive protein levels and/or decreasing blood ESRs.

The non-transitory medium also includes instructions to, in accordance with the executed diet recommendation process, additionally baseline an optimal blood LDL level and an optimal blood C-reactive protein level and/or an optimal blood ESR based on the performance of the statistical analyses, determine that adhering to the baselined optimized diet to be recommended to the user results in an increase in the elevated blood LDL level of the user accompanied by a decrease in the elevated blood C-reactive protein level and/or a decrease in the elevated blood ESR thereof, and modify a composition of the baselined optimized diet to be recommended to the user based on the determined increase in the elevated blood LDL level of the user accompanied by the decrease in the elevated blood C-reactive protein level and/or the decrease in the elevated blood ESR thereof and one or more parameter(s) of the user with reference to the additionally baselined optimal blood LDL level and the optimal blood C-reactive protein level and/or the optimal blood ESR.

The methods and systems disclosed herein may be implemented in any means for achieving various aspects, and may be executed in a form of a machine-readable medium embodying a set of instructions that, when executed by a machine, causes the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of accompanying drawings, in which like references indicate similar elements and in which.

Other features of the present embodiments will be apparent from the accompanying drawings and from the detailed description that follows.

DETAILED DESCRIPTION

Example embodiments, as described below, may be used to provide a ketogenic diet recommendation to a user based on a blood low-density lipoprotein (LDL) level and a blood C-reactive protein level and/or a blood Erythrocyte Sedimentation Rate (ESR) thereof. It will be appreciated that the various embodiments discussed herein need not necessarily belong to the same group of exemplary embodiments, and may be grouped into various other embodiments not explicitly disclosed herein. In the following description, for purposes of explanation, numerous specific details are set forth in order to provide a thorough understanding of the various embodiments.

Figure 1:
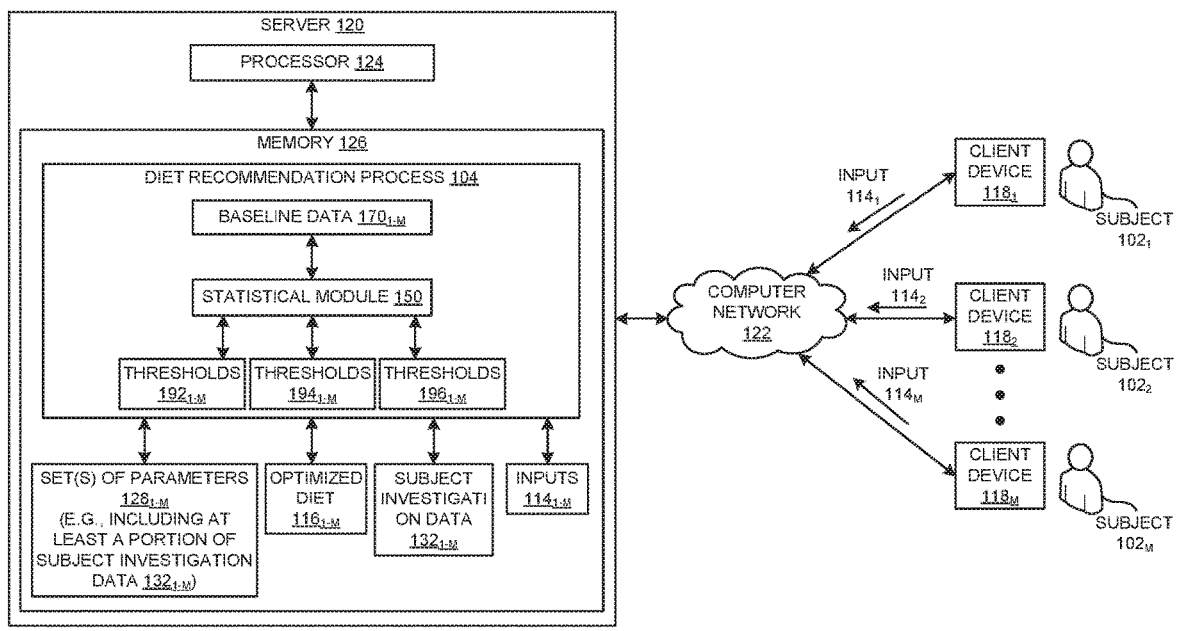
FIG. 1 is a schematic view of human subjects interacting with a diet recommendation process implemented through a server, according to one or more embodiments.

FIG. 1 shows interaction of a subject $102_{1-M}$ (e.g., a human being, a mammal) with a diet recommendation process 104, according to one or more embodiments. In one or more embodiments, diet recommendation process 104 may be designed and/or recommended by a medical professional 106 (e.g., a doctor) and/or a nutritionist and/or may be incorporated into a commercial product 110 by an entity 112 (e.g., a consumer goods company). In one or more embodiments, diet recommendation process 104 may be the basis for design of commercial product 110; in other words, diet recommendation process 104 may inform ingredients of commercial product 110 and proportions thereof within commercial product 110.

In one example scenario, commercial product 110 may be a health drink or a packaged meal. Here, based on diet recommendation process 104, the proportion of macronutrients, viz. proteins, fats and carbohydrates to be within commercial product 110 may be determined. An example proportion may be approximately 75% fats including organic saturated fats, approximately 20% proteins and a maximum of 5% carbohydrates. Appropriate choices of foods corresponding to the aforementioned example proportion may be determined by entity 112 based on a market thereof to launch a new commercial product 110 and/or to implement a health improvement on an existing commercial product 110.

FIG. 1 shows a number of subjects $102_{1-M}$ (or, a population of human subjects $102_{1-M}$) subjected to diet recommendation process 104, according to one or more embodiments. In one or more embodiments, diet recommendation process 104 may be implemented on subjects $102_{1-M}$ for the purpose of optimizing body weight thereof; other purposes of diet recommendation process 104, such as reversing insulin resistance and improving cardiovascular health, are within the scope of the exemplary embodiments discussed herein. In one or more embodiments, diet recommendation process 104 may take a set of inputs $114_{1-M}$ from each subject $102_{1-M}$ to perform analyses relevant to recommending an optimized diet $116_{1-M}$ thereto.

FIG. 1 shows each subject $102_{1-M}$ at a corresponding client device $118_{1-M}$. In one or more embodiments, each client device $118_{1-M}$ may be a data processing device such as a desktop computer, a laptop, a notebook, a mobile device (e.g., mobile phone, smart music device, a smart watch, a smart band) and a tablet communicatively coupled to a server 120 configured to execute diet recommendation process 104 through a computer network 122. Other forms of data processing devices representing client devices $118_{1-M}$ are within the scope of the exemplary embodiments discussed herein. FIG. 1 shows server 120 including a processor 124 (e.g., a microprocessor, Central Processing Unit (CPU), a Graphics Processing Unit (GPU), a cluster of processors) communicatively coupled to a memory 126, according to one or more embodiments; memory 126 may include storage locations configured to be addressable by processor 124.

In one or more embodiments, memory 126 may include instructions associated with diet recommendation process 104 stored therein and configured to be executable through processor 124; for the aforementioned purpose, FIG. 1 shows diet recommendation process 104 stored in memory 126; inputs $114_{1-M}$ from each subject $102_{1-M}$ (e.g., from a corresponding client device $118_{1-M}$) may also be stored in memory 126 to be used by diet recommendation process 104. In one or more embodiments, computer network 122 may be a Wide Area Network (WAN) (e.g., Internet), a Local Area Network (LAN) or a short range network (e.g., Bluetooth®). Other forms of computer network 122 are within the scope of the exemplary embodiments discussed herein.

Concepts associated with diet recommendation process 104 will be discussed below to provide context thereto. Losing weight, reversing insulin resistance, improving cardiovascular health et al. may require establishing what a current diet of a subject $102_{1-M}$ is, along with parameters associated therewith such as age, height, weight, activity levels and target weight loss. In one or more embodiments, sets of parameters $128_{1-M}$ may be associated with the aforementioned subjects $102_{1-M}$. For the sake of simplicity and convenience, sets of parameters $128_{1-M}$ may include all of the above parameters and the current diet information; said sets of parameters $128_{1-M}$, again, may be stored in memory 126.

A diet including a significant portion of carbohydrates (e.g., refined carbohydrates) may have harmful effects on a human body. For example, a high intake of sugar may lead to increased prevalence of metabolic syndrome and obesity and an increased probability of developing diabetes mellitus. Typically, a ketogenic diet, which is a low carbohydrate, high fat diet may be recommended for weight loss enthusiasts, diabetics and pre-diabetics and those with heart disease. As the aforementioned ketogenic diet may involve a reduced carbohydrate intake and substitution of carbohydrates with fat, a body of subject $102_{1-M}$ under said ketogenic diet may experience ketosis, a state in which fats are burned instead of glucose for energy, especially during periods of low blood sugar. Thus, adherence to the ketogenic diet may help subject $102_{1-M}$ maintain a healthy weight and a Body Mass Index (BMI) over the long term. Studies have noted the significant reduction in blood glucose levels following weeks of treatment with ketogenic diets.

Low-density lipoprotein (LDL) is a combination of fat (lipid) and protein. LDLs move freely through blood within the human body due to binding thereof to proteins. LDL is often regarded as "bad" cholesterol due to alleged negative effects thereof on cardiovascular health. However, studies indicate no association between LDL levels and negative cardiovascular health risks. The perception of LDL levels as contributing to decreased cardiovascular health may be due to overlooked factors such as mental stress that can raise cholesterol levels and cause hypertension or platelet aggregation.

Several ketogenic diets may be available that differ in composition of protein, fat and carbohydrate therein. Examples of ketogenic diets may include but are not limited to a classical ketogenic diet, a medium chain triglyceride (MCT) diet, a low glycemic index diet and a modified Atkins diet. Each of the aforesaid diets may differ in compositions thereof; therefore, different benefits may ensue from individual ketogenic diets based on the ratio of macronutrients therein and the range of foods consumed. For example, the classical ketogenic diet includes consistent foods, which results in little variation in ketones; however, a diet that is higher in protein such as an MCT based one may allow for a greater volume to mix different kinds of fats.

Exemplary embodiments may provide for control of a composition of a ketogenic diet based on studying the effects of a ketogenic diet on subjects $102_{1-M}$ (e.g., males and/or females) with elevated blood LDL levels in the mid-range, or, mildly elevated blood LDL levels (e.g., 100-150 milligrams per deciliter (mg/dL)) and elevated blood C-reactive protein levels (e.g., >3 mg per liter (mg/L)) and/or elevated blood Erythrocyte Sedimentation Rates (ESR) (e.g., >20 millimeters per hour). It should be noted that blood C-reactive protein levels may usually be correlated with blood ESRs. Analyses associated with exemplary embodiments may indicate that the ketogenic diet may cause a shift of small dense LDL to large buoyant LDL, which reduces negative risks associated with cardiovascular health. In one or more embodiments, based on investigation of subjects $102_{1-M}$, periods of higher blood LDL levels may have positive impacts on cardiovascular health and inflammation.

In one or more embodiments, on a ketogenic diet, while cholesterol levels may be elevated, said cholesterol levels may be accompanied by extremely low levels of C-reactive proteins in the blood of subjects $102_{1-M}$. High blood LDL levels in subjects $102_{1-M}$ may typically be associated with build-up of plaque on arterial walls thereof. Plaque may be made up of cholesterol, calcium and other substances, and may be undesirable because of the possibility of narrowed arteries, which obstruct the normal flow of blood. Plates of plaque breaking away from the arterial walls may form lumps in the bloodstream that may cause stroke or heart attacks.

However, in order for plaque to be detached, inflammation may need to occur at a release site thereof. The aforementioned inflammation may have a high C-reactive protein score associated therewith, which is contrary to the extremely low levels of C-reactive proteins in the blood of subjects $102_{1-M}$ discussed above. Moreover, in one or more embodiments, calcification in the bloodstream of subjects $102_{1-M}$ fed on specific ketogenic diets may not occur. Further, in one or more embodiments, subjects $102_{1-M}$ may not show visual evidence of blockage or damage to veins and arteries.

Figure 2:
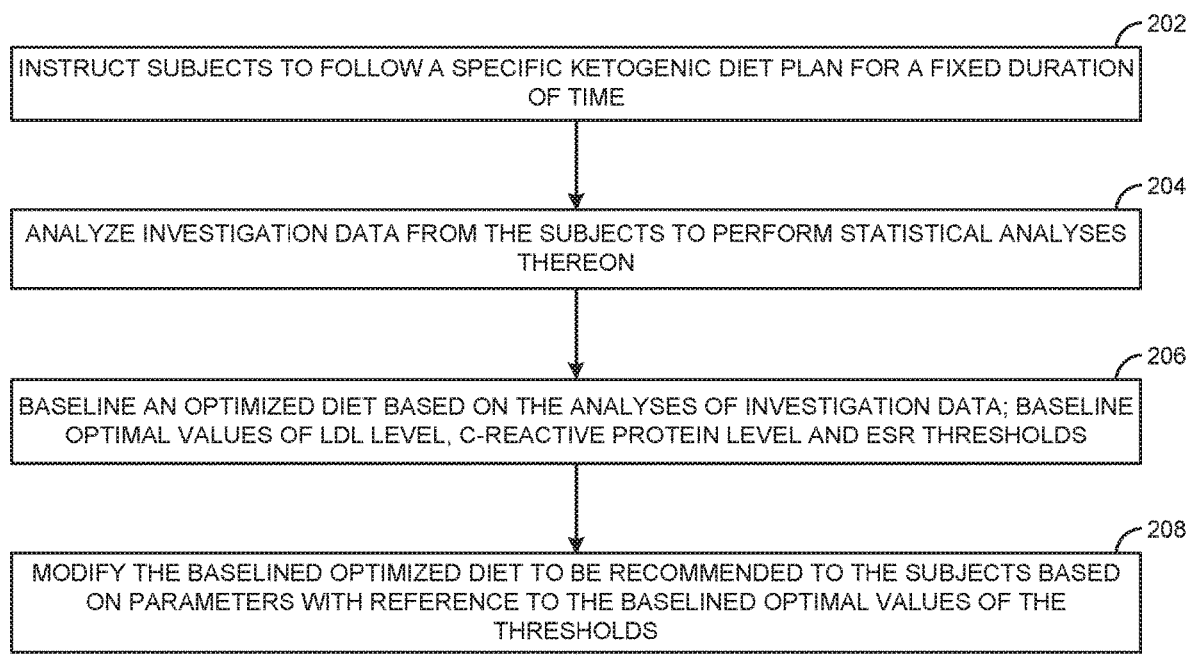
FIG. 2 is a process flow diagram detailing the operations involved in investigating effects of a ketogenic diet on the human subjects of FIG. 1, according to one or more embodiments.

FIG. 2 shows a process flow diagram detailing the operations involved in investigating effects of a ketogenic diet on subjects $102_{1-M}$, according to one or more embodiments. In one or more embodiments, operation 202 may involve server 120 instructing subjects $102_{1-M}$ to follow a specific ketogenic diet plan for a fixed duration of time (e.g., 168 days) in accordance with diet recommendation process 104. In one or more embodiments, in accordance with diet recommendation process 104, server 120 may also advice subjects $102_{1-M}$ to record results from ketone and glucose monitors for determination of compliance therewith.

In one example implementation of diet recommendation process 104, subjects $102_{1-M}$ may be advised not to exceed consumption of 1400 to 1800 calories from fat, which may correspond to 156 grams of fat, 500 calories from protein, which may correspond to 125 grams of protein and 80 calories from carbohydrates, which may correspond to 20 grams, per day. Here, a concomitant diet plan providing guidelines of foods to be consumed and not consumed may be made available to subjects $102_{1-M}$.

In one or more embodiments, prior to the recommendation of the specific ketogenic diet plan in operation 202, subjects $102_{1-M}$ may be screened in accordance with diet recommendation process 104. In one or more embodiments, example screening assessments may include but are not limited to review of medical history and current health status, assessment of inclusion and exclusion criteria, review of pre-existing medications, supplements and diet(s), urine pregnancy test for female subjects $102_{1-M}$ with child-bearing potential, height and weight measurements, BMI, seated resting blood pressure and heart rate measurements, fasting blood samples for specific analyses (e.g., Complete Blood Count (CBC), electrolytes (e.g., $Na^+$, $K^+$, $Cl^-$, P), HbA1c, glucose, creatinine, Aspartate Aminotransferase (AST), Alanine Transaminase (ALT), total bilirubin, lipid panel and Thyroid Stimulating Harmone (TSH) levels). In one or more embodiments, subjects $102_{1-M}$ may be instructed to maintain similar levels of physical activity in order to provide for accurate baseline data (e.g., baseline data $170_{1-M}$) on a consistent basis.

In one or more embodiments, the screening discussed above may include a baselining operation, in which eligible subjects $102_{1-M}$ may return for baseline assessments after a 12 hour fasting period. In one or more embodiments, the aforementioned baseline assessments may include collecting and reviewing food records, assessing inclusion and exclusion criteria, performing physical examinations, reviewing pre-existing therapies and current health statuses, urine pregnancy tests for female potential subjects $102_{1-M}$ that are of child-bearing potential, weight measurements and BMI calculations, seated resting blood pressure and heart rate measurements, Electrocardiogram (ECG) and total body Dual-Energy X-ray Absorptiometry (DEXA) scans, collection of fasting blood for analysis of glucose levels, HbA1c, C-reactive protein levels, lipid panel, free triiodothyronine (T3), Erythrocyte Sedimentation Rate (ESR) and androstenedione.

The abovementioned baselining operation may be accompanied by nutritional counseling about the specific ketogenic diet plan discussed above, the dispensing of glucose monitors and/or ketone monitors and instructions on use thereof, and re-dispensing food records of subjects $102_{1-M}$. Thus, in one or more embodiments, the screening process including the baselining operation may occupy the first two days of the investigation of the effects of the ketogenic diet on subjects $102_{1-M}$. It should be noted that while one or more subjects $102_{1-M}$ may be declared as ineligible for the investigation in accordance with the processes discussed above, all subjects $102_{1-M}$ discussed with respect to FIG. 1 that form part of subsequent discussion(s) may be regarded as "eligible" subjects for the sake of convenience.

In one or more embodiments, subsequent visits for assessment may involve collection and review of subject treatment diaries, collection and review of food records, performing compliance calculations, review concomitant therapies and adverse events, resting blood pressure and heart rate measurements, weight measurements and BMI calculations, total body DEXA scans and ECG tests, lipid panel analyses based on collecting blood samples, re-dispensing food records, re-dispensing subject treatment diaries and so on. In one or more embodiments, during each visit, subjects $102_{1-M}$ may be reminded to return to the location of assessment (e.g., a clinic) for the subsequent visit following fasting for 12 hours, to complete food records thereof, to abide by medication instructions, to submit completed subject treatment diaries and to maintain consistency in physical activity and diet.

In one or more embodiments, the investigation may end (e.g., on day 168±3) with subjects $102_{1-M}$ returning to the location of assessment after fasting for 12 hours to complete assessments thereof with completed food records and subject treatment diaries. In one or more embodiments, the end assessments may include collecting and reviewing subject treatments diaries, collecting and reviewing food records, performance compliance calculations, collecting and reviewing glucose and ketone monitors, reviewing concomitant therapies and adverse events, weight measurements, BMI calculations, seated resting blood pressure and heart rate measurements, ECG tests and total body DEXA scans, collecting fasting blood samples for analyses of CBC, electrolytes (e.g., $Na^+$, $K^+$, $Cl^-$, P), HbA1c, glucose, estimated Glomerular Filtration Rate (eGFR), creatinine, AST, ALT and total bilirubin, collecting blood for analyses of fasting glucose, HbA1c, C-reactive protein, lipid panel, free T3, ESR and androstenedione.

In one or more embodiments, operation 204 may involve server 120 analyzing the abovementioned investigation data from subjects $202_{1-M}$ to perform statistical analyses thereon. FIG. 1 shows the abovementioned investigation data as subject investigation data $132_{1-M}$, according to one or more embodiments; said subject investigation data $132_{1-M}$ is shown as stored in memory 126 of server 120. In one or more embodiments, statistical analyses on subject investigation data $132_{1-M}$ may be implemented through diet recommendation process 104 including tests of significance (e.g., two tailed tests, with alpha levels of, say, 0.05). In one example implementation, all primary and secondary endpoints of the investigation may be analyzed as continuous variables. For each primary and secondary endpoint, said descriptive statistics may include number of subjects, arithmetic mean, standard deviation, median, minimum and maximum values presented for each day of investigation and for changes from the baseline day to each subsequent day of visit.

In one or more embodiments, changes in continuous endpoints may be computed and analyzed based on Mixed Model for Repeated Measures (MMRM). MMRM is known to one skilled in the art. Detailed discussion associated therewith has, therefore, been skipped for the sake of convenience and clarity. In one or more embodiments, the aforementioned model may include baseline values (e.g., baseline data $170_{1-M}$) and values related to scheduled visits as independent variables. In one or more embodiments, p-values for changes from the baseline may be obtained from the model. In one or more embodiments, no adjustments on p-values for multiple primary endpoints may be made. In one or more embodiments, with regard to subjects $102_{1-M}$ dropping out of the investigation mid-way and/or missing data for primary and second endpoints, a Last Observation Carried Forward (LOCF) method or an Intention To Treat (ITT) analysis based on multiple imputation may be utilized.

In one or more embodiments, a statistical module 150 implemented through diet recommendation process 104 stored in memory 126 may perform all of the abovementioned statistical analyses on subject investigation data $132_{1-M}$. Primary and secondary endpoints with respect to clinical investigations may be well known to one skilled in the art. Detailed discussion associated therewith has, therefore, been skipped for the sake of convenience and clarity.

In one example scenario, the primary endpoint may be increasing LDL levels in subjects $102_{1-M}$ and the secondary endpoints may be the concomitantly decreasing C-reactive protein levels and/or ESRs thereof. In one or more embodiments, statistical analyses implemented through statistical module 150 may confirm that for subjects $102_{1-M}$ with mildly elevated blood LDL levels (e.g., 100-150 milligrams per deciliter (mg/dL)) and mildly elevated blood C-reactive protein levels (e.g. >3 mg per liter (mg/L)) and/or mildly elevated blood ESRs (e.g., >20 millimeters per hour (mm/hr)), a specific ketogenic diet plan (e.g., 75% fat including a lot of organic saturated fat, 20% of protein and a maximum of 5% carbohydrates) may lead to rising LDL levels accompanied by dropping C-reactive protein levels and/or ESRs.

In one or more embodiments, as it is medically agreed that lower C-reactive protein and ESRs are signs of better cardiovascular health, recommending the abovementioned ketogenic diet as part of diet recommendation process 104 may result in healthier subjects $102_{1-M}$. In one or more embodiments, recommending a ketogenic diet that increases LDL levels may be counterintuitive (and, thereby, non-obvious), especially with regard to received nutritional wisdom.

In one or more embodiments, at least a portion of subject investigation data $132_{1-M}$ may form part of sets of parameters $128_{1-M}$ associated with subjects $102_{1-M}$. Thus, in one or more embodiments, optimized diet $116_{1-M}$ may be made available to subjects $102_{1-M}$ based on tweaking the ketogenic diet recommended above in accordance with parameters $128_{1-M}$. It should be noted that subjects $102_{1-M}$ part of the investigation discussed above may be different from subjects $102_{1-M}$ to which optimized diet $116_{1-M}$ is recommended. FIGS. 1 and 2 and discussion associated therewith regard both as the same for the sake of convenience and clarity.

For example, subjects $102_{1-M}$ that are investigated may be utilized to confirm the benefits of the ketogenic diet discussed above by determining that increasing blood LDL levels are accompanied by decreasing blood C-reactive protein levels and/or blood ESRs. In one or more embodiments, the ketogenic diet discussed above may be modified to effect the benefits of decreasing C-reactive protein levels and/or ESRs. FIG. 1 shows LDL level thresholds $192_{1-M}$ associated with subjects $102_{1-M}$ that are tolerated, along with thresholds $194_{1-M}$ below which blood C-reactive protein levels are desirable in subjects $102_{1-M}$ and thresholds $196_{1-M}$ below which blood ESRs are desirable in subjects $102_{1-M}$ based on the statistical analyses discussed above. Referring back to FIG. 2, operation 206 may involve baselining optimized diet $116_{1-M}$ based on the aforementioned investigation of subjects $102_{1-M}$; operation 206 may also involve baselining optimal values of thresholds $192_{1-M}$ and thresholds $194_{1-M}$ and/or thresholds $196_{1-M}$ based on the investigation discussed above.

As discussed above, optimized diet $116_{1-M}$ may be recommended to a different set of subjects than subjects $102_{1-M}$. However, for the sake of convenience, subjects $102_{1-M}$ to whom optimized diet $116_{1-M}$ is recommended may be the same investigated subjects $102_{1-M}$. Now, in one or more embodiments, operation 208 may then involve modifying optimized diet $116_{1-M}$ to be recommended to subjects $102_{1-M}$ based on parameters $128_{1-M}$ with reference to baselined values of thresholds $192_{1-M}$ and thresholds $194_{1-M}$ and/or thresholds $196_{1-M}$ thereof. For example, diet recommendation process 104 may determine that baselined thresholds $192_{1-M}$, thresholds $194_{1-M}$ and/or thresholds $196_{1-M}$ may need to be modified based on parameters $128_{1-M}$ associated with a subject $102_{1-M}$. Thus, optimized diet $116_{1-M}$ may also be required to be modified for subject $102_{1-M}$.

In one or more embodiments, the abovementioned modification of optimized diet $116_{1-M}$ may involve changing composition of proteins, fat and carbohydrates therein. For example, based on parameters $128_{1-M}$, a baseline optimized diet of 75% fat, 20% of protein and a maximum of 5% carbohydrates may be modified into 73% fat, 23% protein and a maximum of 4% carbohydrates for a subject $102_{1-M}$. It should be noted that the modification of the composition of optimized diet $116_{1-M}$ may also be accompanied by a modification of one or more type(s)/source(s) of food representing said composition (e.g., in the case of proteins, a larger portion of fish may be recommended instead of or in addition to a portion of beef). In one or more embodiments, a maximum value of the carbohydrates may still be 5% of the composition of optimized diet $116_{1-M}$ for all subjects $102_{1-M}$. All reasonable variations are within the scope of the exemplary embodiments discussed herein.

In one or more embodiments, all operations associated with the investigation of subject(s) $102_{1-M}$, the recommendation of optimized diet $116_{1-M}$, the baselining of optimized diet $116_{1-M}$/thresholds $192_{1-M}$/thresholds $194_{1-M}$/thresholds $196_{1-M}$, and the modification of optimized diet $116_{1-M}$ may be performed through server 120 based on execution of diet recommendation process 104. It should be noted that any data processing device may be interpretable as server 120. One or more operations may also be performed through server 120 in conjunction with authorized personnel (e.g., doctors, nutritionists, medical staff, nutritional staff). Thus, exemplary embodiments provide a means for recommending a ketogenic diet to users with mildly elevated blood LDL levels and blood C-reactive protein levels and/or blood ESRs to facilitate increases in the mildly elevated blood LDL levels that are accompanied by decreasing blood C-reactive protein levels and/or blood ESRs; the aforementioned recommendation, therefore, runs counter to traditional medical and nutritional wisdom.

Further, instructions associated with diet recommendation process 104 may be tangibly embodied on a non-transitory medium (e.g., Compact Disc (CD), Digital Video Disc (DVD), a Blu-ray Disc®, a hard disk/drive) readable through server 120 and/or client device(s) $118_{1-M}$ and configured to be executable therethrough. Also, it should be noted that medical procedures/tests/operations to measure/determine blood LDL levels, blood C-reactive protein levels and blood ESRs are known to one skilled in the art. Detailed discussion associated therewith has, therefore, been skipped for the sake of convenience. All reasonable variations are within the scope of the exemplary embodiments discussed herein.

Figure 3:
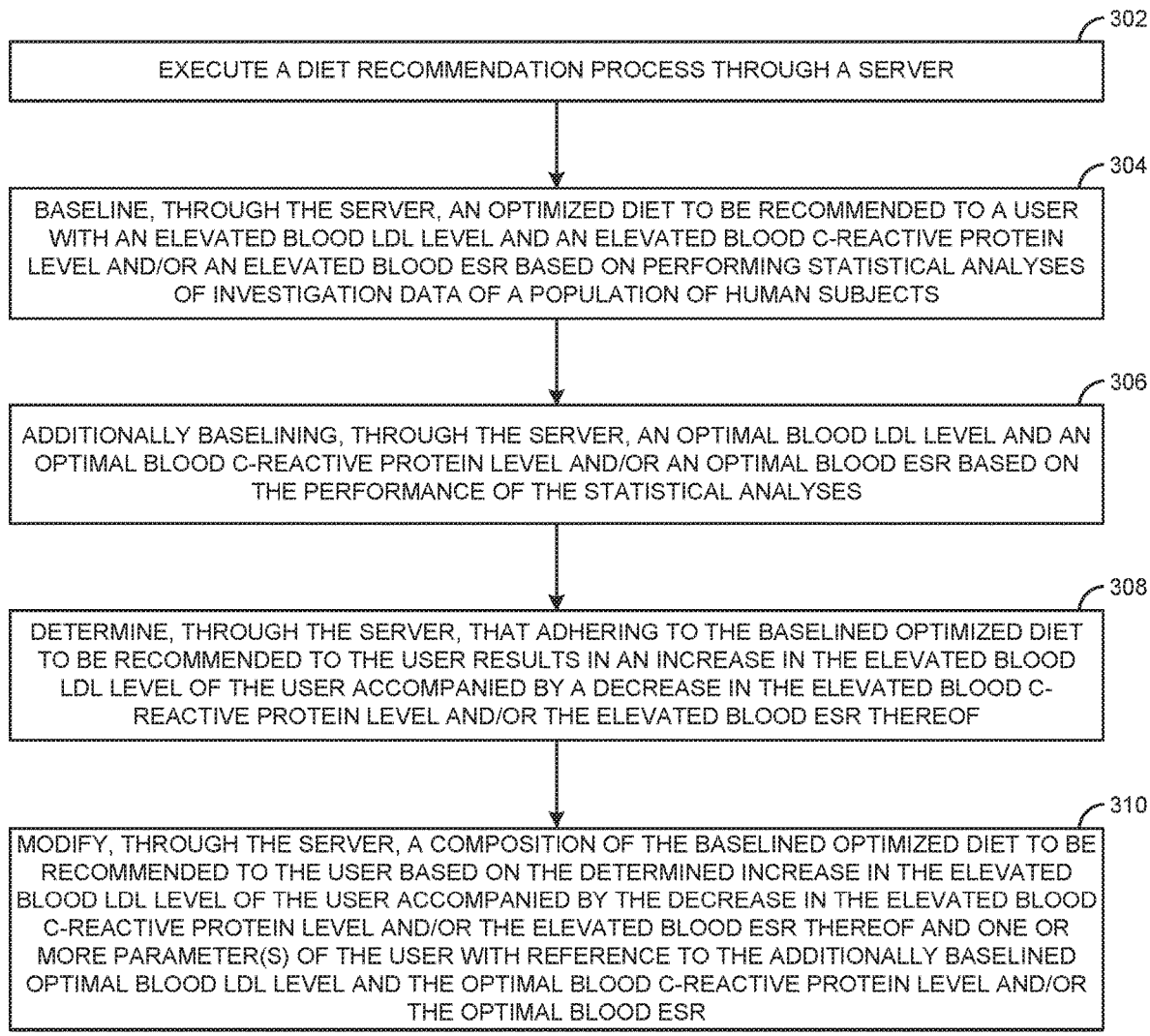
FIG. 3 is a process flow diagram detailing the operations involved in a ketogenic diet recommendation to a user based on a blood low-density lipoprotein (LDL) level and a blood C-reactive protein level and/or a blood Erythrocyte Sedimentation Rate (ESR) thereof, according to one or more embodiments.

FIG. 3 shows a process flow diagram detailing the operations involved in a ketogenic diet (e.g., optimized diet $116_{1-M}$) recommendation to a user (e.g., a subject $102_{1-M}$) based on a blood LDL level and a blood C-reactive protein level and/or a blood ESR thereof, according to one or more embodiments. In one or more embodiments, operation 302 may involve executing a diet recommendation process (e.g., diet recommendation process 104) through a server (e.g., server 120).

In one or more embodiments, operation 304 may involve, in accordance with the executed diet recommendation process, baselining, through the server, an optimized diet (e.g., optimized diet $116_{1-M}$) to be recommended to the user with an elevated blood LDL level of 100-150 milligrams per deciliter (mg/dL) and an elevated blood C-reactive protein level of >3 mg/L and/or an elevated blood ESR of >20 millimeters per hour (mm/hr) based on performing statistical analyses (e.g., through statistical module 150) on investigation data (e.g., subject investigation data $132_{1-M}$) of a population of human subjects (e.g., subjects $102_{1-M}$) with elevated blood LDL levels of 100-150 mg/dL and elevated blood C-reactive protein levels of >3 mg/L and/or elevated blood ESRs of >20 mm/hr to determine that adhering to the optimized diet leads to increasing blood LDL levels for the population accompanied by decreasing blood C-reactive protein levels and/or decreasing blood ESRs.

In one or more embodiments, operation 306 may involve additionally baselining, through the server, an optimal blood LDL level (e.g., an optimal value of threshold $192_{1-M}$) and an optimal blood C-reactive protein level (e.g., an optimal value of threshold $194_{1-M}$) and/or an optimal blood ESR (e.g., an optimal value of threshold $196_{1-M}$) based on the performance of the statistical analyses. In one or more embodiments, operation 308 may involve determining, through the server, that adhering to the baselined optimized diet to be recommended to the user results in an increase in the elevated blood LDL level of the user accompanied by a decrease in the elevated blood C-reactive protein level and/or a decrease in the elevated blood ESR thereof. In one or more embodiments, operation 310 may then involve modifying, through the server, a composition of the baselined optimized diet to be recommended to the user based on the determined increase in the elevated blood LDL level of the user accompanied by the decrease in the elevated blood C-reactive protein level and/or the decrease in the elevated blood ESR thereof and one or more parameter(s) (e.g., parameter(s) $128_{1-M}$) of the user with reference to the additionally baselined optimal blood LDL level and the optimal blood C-reactive protein level and/or the optimal blood ESR.

Although the present embodiments have been described with reference to specific example embodiments, it will be evident that various modifications and changes may be made to these embodiments without departing from the broader spirit and scope of the various embodiments. For example, the various devices and modules described herein may be enabled and operated using hardware circuitry (e.g., CMOS based logic circuitry), firmware, software or any combination of hardware, firmware, and software (e.g., embodied in a machine readable medium). For example, the various electrical structures and methods may be embodied using transistors, logic gates, and electrical circuits (e.g., application specific integrated (ASIC) circuitry and/or in Digital Signal Processor (DSP) circuitry).

In addition, it will be appreciated that the various operations, processes, and methods disclosed herein may be embodied in a machine-readable medium and/or a machine accessible medium compatible with a data processing system (e.g., server 120, client devices $118_{1-M}$), and may be performed in any order (e.g., including using means for achieving the various operations). Accordingly, the specification and drawings are to be regarded in an illustrative rather than a restrictive sense.

What is claimed is:

1. A method of optimizing a composition of a food product based on a ketogenic diet recommended to a human subject with an elevated blood low-density lipoprotein (LDL) level of 100-150 milligrams per deciliter (mg/dL) and at least one of: an elevated blood C-reactive protein level of >3 mg/L and an elevated blood Erythrocyte Sedimentation Rate (ESR) of >20 millimeters per hour (mm/hr), comprising:

under at least one of: design and recommendation of a medical professional, administering the ketogenic diet for a duration of time of 168±3 days to a population of investigated human subjects with elevated blood LDL levels of 100-150 mg/dL and at least one of:

elevated blood C-reactive protein levels of >3 mg/L and elevated blood ESRs of >20 mm/hr;

performing, through a processor communicatively coupled to a memory, statistical analyses of investigation data of the population of the investigated human subjects based on:

selecting a primary endpoint of the statistical analyses as increasing blood LDL levels and a secondary endpoint of the statistical analyses as concomitantly at least one of: decreasing blood C-reactive protein levels and decreasing blood ESRs for the population of the investigated human subjects;

analyzing the primary endpoint and the secondary endpoint as continuous variables in the statistical arnalyses, and analyzing changes in the primary endpoint and the secondary endpoint based on a Mixed Model for Repeated Measures (WARM) as part of the statistical analyses; and accounting for at least one of: a subset of the population dropping out of the statistical analyses prior to completion thereof and missing data associated with regard to the primary endpoint and the secondary endpoint by utilizing one of: a Last Observation Carried Forward (LOCF) method and an Intention to Treat (ITT) analysis based on multiple imputation;

determining, through the statistical analyses, that adhering to the ketogenic diet by the population of the investigated human subjects for the duration of time of 168±3 days results in an increase in the elevated blood LDL levels thereof accompanied by at least one of: a decrease in the elevated blood C-reactive protein levels and a decrease in the elevated blood ESRs thereof;

modifying, through the processor, a composition of the ketogenic diet in accordance with the statistical analyses performed based on the determination of the increase in the elevated blood LDL levels of the population of the investigated human subjects accompanied by the at least one of: the decrease in the elevated blood. C-reactive protein levels and the decrease in the elevated blood ESRs thereof; and modifying the composition of the food product based on the ketogenic diet recommended to the human subject in line with the modified composition of the ketogenic diet.

2. The method of claim 1, wherein modifying the composition of the ketogenic diet comprises modifying, through the processor, at least one source of food representing the modified composition of the ketogenic diet.

3. The method of claim 1, comprising the human subject being part of the population of the investigated human subjects.

4. The method of claim 1, comprising the ketogenic diet comprising a maximum of 5% carbohydrates therein.

* * * * *